United States Patent
Zhao et al.

(10) Patent No.: US 11,900,592 B2
(45) Date of Patent: Feb. 13, 2024

(54) METHOD, DEVICE, AND STORAGE MEDIUM FOR PANCREATIC MASS SEGMENTATION, DIAGNOSIS, AND QUANTITATIVE PATIENT MANAGEMENT

(71) Applicant: Ping An Technology (Shenzhen) Co., Ltd., Shenzhen (CN)

(72) Inventors: Tianyi Zhao, Bethesda, MD (US); Kai Cao, Shanghai (CN); Ling Zhang, Bethesda, MD (US); Jiawen Yao, Bethesda, MD (US); Le Lu, Bethesda, MD (US)

(73) Assignee: PING AN TECHNOLOGY (SHENZHEN) CO., LTD., Shenzhen (CN)

(*) Notice: Subject to any disclaimer, the term of this patent is extended or adjusted under 35 U.S.C. 154(b) by 391 days.

(21) Appl. No.: 17/213,343

(22) Filed: Mar. 26, 2021

(65) Prior Publication Data
US 2022/0180506 A1 Jun. 9, 2022

Related U.S. Application Data

(60) Provisional application No. 63/120,773, filed on Dec. 3, 2020.

(51) Int. Cl.
*G06T 7/00* (2017.01)
*G06T 7/11* (2017.01)
(Continued)

(52) U.S. Cl.
CPC ............ *G06T 7/0012* (2013.01); *A61B 5/425* (2013.01); *G06T 7/11* (2017.01); *G06T 17/205* (2013.01);
(Continued)

(58) Field of Classification Search
CPC ... A61B 5/425; A61B 5/7264; A61B 2526/00; G06T 7/0012; G06T 7/11; G06T 17/205;
(Continued)

(56) References Cited

U.S. PATENT DOCUMENTS

| 10,878,219 | B2 * | 12/2020 | Zhou | G06N 3/045 |
| 2007/0211939 | A1 * | 9/2007 | Kaus | G06V 10/7553 |
| | | | | 382/173 |

(Continued)

OTHER PUBLICATIONS

Zhang et al. "Robust Pancreatic Ductal Adenocarcinoma Segmentation with Multi-Institutional Multi-Phase Partially-Annotated CT Scans." arXiv preprint arXiv:2008.10652 (Aug. 24, 2020). (Year: 2020).*

(Continued)

*Primary Examiner* — Katrina R Fujita
(74) *Attorney, Agent, or Firm* — ANOVA LAW GROUP, PLLC

(57) ABSTRACT

A method for pancreatic mass diagnosis and patient management includes: receiving CT images of a pancreas of a patient, the pancreas of the patient including a mass; performing a segmentation process on the CT images of the pancreas and the mass to obtain a segmentation mask of the pancreas and the mass of the patient; performing a mask-to-mesh process on the segmentation mask of the pancreas and the mass of the patient to obtain a mesh model of the pancreas and the mass of the patient; performing a classification process on the mesh model of the pancreas and the mass of the patient to identify a type and a grade of a segmented pancreatic mass; and outputting updated CT images of the pancreas of the patient, the updated CT images including the segmented pancreatic mass highlighted thereon and the type and the grade of the segmented pancreatic mass annotated thereon.

17 Claims, 7 Drawing Sheets

(51) Int. Cl.
  *G06T 17/20* (2006.01)
  *G16H 20/00* (2018.01)
  *A61B 5/00* (2006.01)
(52) U.S. Cl.
  CPC ... *G16H 20/00* (2018.01); *G06T 2207/10081* (2013.01); *G06T 2207/20081* (2013.01); *G06T 2207/20084* (2013.01); *G06T 2207/30004* (2013.01)
(58) Field of Classification Search
  CPC . G06T 2207/10081; G06T 2207/20081; G06T 2207/20084; G06T 2207/30004; G06T 2207/30096; G16H 20/00; G16H 20/40; G16H 30/40; G16H 50/20; G16H 50/50; G16H 50/70
  See application file for complete search history.

(56) References Cited

U.S. PATENT DOCUMENTS

| | | | | |
|---|---|---|---|---|
| 2009/0226060 A1* | 9/2009 | Gering | | G06T 7/174 382/128 |
| 2017/0172450 A1* | 6/2017 | Koay | | A61B 6/032 |
| 2019/0019300 A1* | 1/2019 | Simpson | | G06T 7/40 |
| 2019/0139223 A1* | 5/2019 | Nie | | G06T 7/187 |
| 2019/0333222 A1* | 10/2019 | Gatti | | G06T 7/143 |
| 2021/0279880 A1* | 9/2021 | Giner | | G06T 7/0012 |
| 2021/0397943 A1* | 12/2021 | Ribalta | | G06N 3/08 |
| 2021/0397966 A1* | 12/2021 | Sun | | G06T 7/10 |
| 2022/0005586 A1* | 1/2022 | Brynolfsson | | G06T 7/0012 |

OTHER PUBLICATIONS

Yao et al. "DeepPrognosis: Preoperative Prediction of Pancreatic Cancer Survival and Surgical Margin via Contrast-Enhanced CT Imaging." arXiv preprint arXiv:2008.11853 (Aug. 26, 2020). (Year: 2020).*

Reid et al. "The evolving role of pathology in new developments, classification, terminology, and diagnosis of pancreatobiliary neoplasms." Archives of Pathology & Laboratory Medicine 141.3 (2017): 366-380. (Year: 2017).*

Wei et al. "Computer-aided diagnosis of pancreas serous cystic neoplasms: a radiomics method on preoperative MDCT images." Technology in cancer research & treatment 18 (2019): 1533033818824339. (Year: 2019).*

* cited by examiner

METHOD, DEVICE, AND STORAGE MEDIUM FOR PANCREATIC MASS SEGMENTATION, DIAGNOSIS, AND QUANTITATIVE PATIENT MANAGEMENT

CROSS-REFERENCE TO RELATED APPLICATION

This application claims the priority of U. S. Provisional Patent Application No. 63/120,773, filed on Dec. 3, 2020, the entire content of which is incorporated herein by reference.

FIELD OF THE TECHNOLOGY

This application relates to the field of medical image interpretation and, more particularly, to a method, device, and storage medium for pancreatic mass diagnosis and patient management.

BACKGROUND OF THE DISCLOSURE

Pancreatic cancer is the third leading cause of cancer-related deaths in the United States, yet had the poorest prognosis among all solid malignancies, with a 5-year survival rate at about 10%. Early diagnosis is crucial as it can potentially increase the 5-year survival rate to about 50%. The clinical management of patients with pancreatic disease is based on the potential of the mass to become an invasive cancer. Unlike masses in other organs, pancreatic masses often cannot be reached precisely via needle biopsy due to the pancreas; deep location in the abdomen and the complex network of surrounding organs and vessels. Therefore, reliable imaging-based diagnosis is critical to identifying patients who truly require cancer treatment (e.g., surgery) in a timely fashion, while avoiding unnecessary iatrogenic morbidity. Developing deep learning methods to detect masses, identify malignancies, provide diagnoses and predict cancer prognosis has the potential to revolutionize pancreatic cancer imaging.

SUMMARY

One aspect of the present disclosure provides a method for pancreatic mass diagnosis and patient management. The method includes: receiving computed tomography (CT) images of a pancreas of a patient during a multi-phase CT scan, the CT images including a plurality of three-dimensional (3D) images of the pancreas for each phase of the multiple phases and the pancreas of the patient including a mass; performing a segmentation process on the CT images of the pancreas and the mass to obtain a segmentation mask of the pancreas and the mass of the patient; performing a mask-to-mesh process on the segmentation mask of the pancreas and the mass of the patient to obtain a mesh model of the pancreas and the mass of the patient; performing a classification process on the mesh model of the pancreas and the mass of the patient to identify a type and a grade of a segmented pancreatic mass; and outputting updated CT images of the pancreas of the patient, the updated CT images including the segmented pancreatic mass highlighted thereon and the type and the grade of the segmented pancreatic mass annotated thereon.

Another aspect of the present disclosure provides a device for pancreatic mass diagnosis and patient management The device includes a memory storing a computer program and a processor configured to execute the computer program stored in the memory to: receive computed tomography (CT) images of a pancreas of a patient during a multi-phase CT scan, the CT images including a plurality of three-dimensional (3D) images of the pancreas for each phase of the multiple phases and the pancreas of the patient including a mass; perform a segmentation process on the CT images of the pancreas and the mass to obtain a segmentation mask of the pancreas the mass of the patient; perform a mask-to-mesh process on the segmentation mask of the pancreas of the patient to obtain a mesh model including 156 vertices of the pancreas of the patient; perform a classification process on the mesh model of the pancreas of the patient to identify a type and a grade of a segmented pancreatic mass; and output updated CT images of the pancreas of the patient, the updated CT images including the segmented pancreatic mass highlighted thereon and the type and the grade of the segmented pancreatic mass annotated thereon.

Another aspect of the present disclosure provides a storage medium storing a computer program. When being executed by a processor, the computer program performs: receiving computed tomography (CT) images of a pancreas of a patient during a multi-phase CT scan, the CT images including a plurality of three-dimensional (3D) images of the pancreas for each phase of the multiple phases and the pancreas of the patient including a mass; performing a segmentation process on the CT images of the pancreas and the mass to obtain a segmentation mask of the pancreas and the mass of the patient; performing a mask-to-mesh process on the segmentation mask of the pancreas and the mass of the patient to obtain a mesh model of the pancreas and the mass of the patient; performing a classification process on the mesh model of the pancreas and the mass of the patient to identify a type and a grade of a segmented pancreatic mass; and outputting updated CT images of the pancreas of the patient, the updated CT images including the segmented pancreatic mass highlighted thereon and the type and the grade of the segmented pancreatic mass annotated thereon.

Other aspects of the present disclosure can be understood by those skilled in the art in light of the description, the claims, and the drawings of the present disclosure.

DETAILED DESCRIPTION

The following describes the technical solutions in the embodiments of the present invention with reference to the accompanying drawings. Wherever possible, the same reference numbers will be used throughout the drawings to refer to the same or like parts. Apparently, the described embodiments are merely some but not all the embodiments of the present invention. Other embodiments obtained by a person skilled in the art based on the embodiments of the present invention without creative efforts shall fall within the protection scope of the present disclosure.

Figure 1:
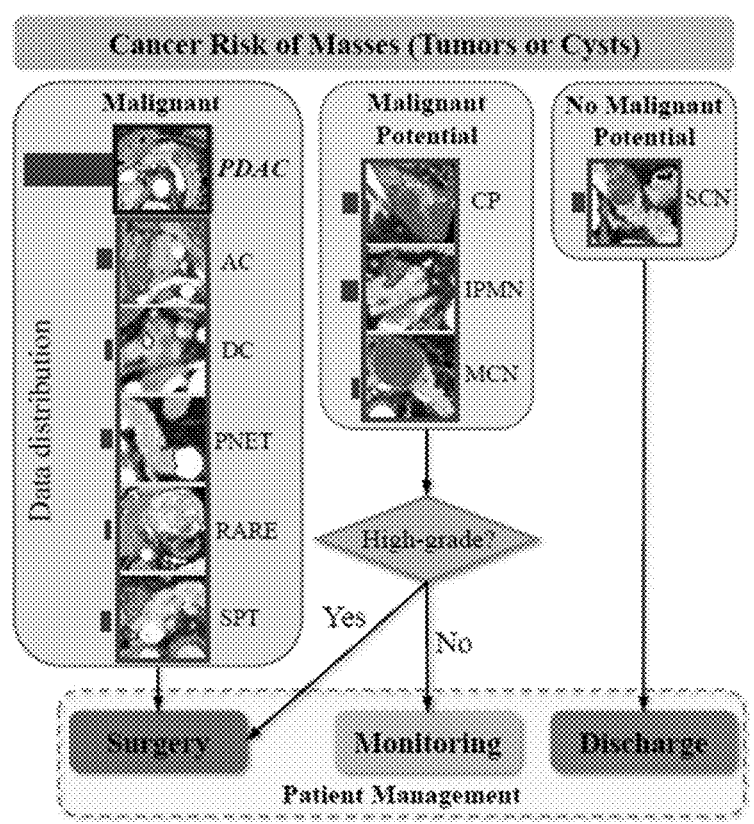
FIG. 1 illustrates a schematic diagram of disease taxonomy of the ten types of pancreatic masses consistent with embodiments of the present disclosure.

FIG. 1 illustrates a schematic diagram of disease taxonomy of the ten types of pancreatic masses consistent with embodiments of the present disclosure. As shown in FIG. 1, the pancreatic disease taxonomy includes ten types of pancreatic masses (also known as tumors or cysts). Segmentation or classification methods have been developed to focus on certain mass types. Differential diagnosis of all mass types is clinically highly desirable but has not been investigated using an automated image understanding approach.

As shown in FIG. 1, a treatment recommendation is provided based on a degree of malignancy of the segmented pancreatic mass. The type of the segmented pancreatic mass includes pancreatic ductal adenocarcinoma (PDAC), ampullary cancer (AC), bile duct cancer (DC), pancreatic neuroendocrine tumor (PNET), rare neo-plasma (RARE), solid pseudopapillary tumor (SPT), chronic pancreatitis (CP), intraductal papillary mucinous neoplasm (IPMN), mucinous cystic neoplasm (MCN), and serous cystic neoplasm (SCN). The grade of the segmented pancreatic mass includes a low grade, an intermediate grade, and a high grade. PDAC, AC, DC, PNET, RARE, and SPT are malignant types, CP, IPMN, and MCN are potentially malignant types, and SCN is a non-malignant type. The patient with the malignant types and the potentially malignant types with the high grade need immediate treatment, the patient with the potentially malignant types with the low and intermediate grades need monitoring, and the patient with the non-malignant type is discharged. Pancreatic mass type diagnosis determines a clinical malignancy indication that leads to proper patient risk stratification and management. The histogram bars on the left side of the pancreatic mass images represent their relative frequencies. All pancreatic mass images are in the arterial-late CT phase.

In the present disclosure, the most common pancreatic ductal adenocarcinoma (PDAC) is distinguished from the nine other non-PDAC masses using multi-phase computed tomography (CT) imaging. Both image appearance and three-dimensional (3D) organ-mass geometry relationship are critical. The present disclosure provides a holistic segmentation-mesh-classification network (SMCN) method to perform a patient level diagnosis, by fully utilizing geometry and location information of the pancreatic mass. The patient level diagnosis is accomplished by combining the anatomical structure and the semantic detect-by-segmentation network. The SMCN method learns various pancreas in a mass segmentation task, builds an anatomical correspondence-aware organ mesh model by progressively deforming a pancreas prototype on a raw segmentation mask (i.e., mask-to-mesh).

In the present disclosure, a graph-based residual convolutional network (Graph-ResNet) is provided to produce patient level differential classification results. Nodes of the Graph-ResNet fuse information of a mesh model and feature vectors extracted from a segmentation network. The SMCN method is used to process 661 patients' CT scans (five phases per patient). The pancreatic mass segmentation and detection accuracy are improved as compared to a baseline method nnUNet. For example, for non-PDAC masses, a dice score of 0.611 is achieved by the SMCN versus the dice score of 0.478 achieved by the baseline method nnUNet, and a detection rate of 89% is achieved by the SMCN versus the detection rate of 70% achieved by the baseline method nnUNet. The SMCN method also achieves sensitivity (e.g., 94%) and specificity (90%) in differentiating PDAC masses and non-PDAC masses similar to expert radiologists. Further, the SMCN method obtains results comparable to a multimodality test that combines clinical, imaging, and molecular testing for clinical management of patients.

In the description of the present disclosure, the PDAC masses and the non-PDAC masses may be shortened the PDAC and the non-PDAC, respectively. Similarly, other types of the pancreatic masses may also be described by their corresponding acronyms.

Multi-phase CT is a first-line imaging modality for the diagnosis of pancreatic disease. Differential diagnosis of pancreatic masses is challenging for several reasons. The same type of pancreatic masses may appear in different textures, shapes, contrasts, and different enhancement patterns across multiple CT phases. The PDAC masses account for most cases in pancreatic cancer specialized hospitals, causing a long-tail problem. Masses, sometimes are surrounded by inflamed tissues and thus cannot be easily identified.

In the embodiments of the present disclosure, the SMCN method tackles two problems with strong clinical indications, which include PDAC versus non-PDAC differentiation and clinical management of patients. PDAC is a unique group with the most dismal prognosis. Distinguishing PDAC from non-PDACs is always an objective. The patient management includes three recommendations including surgery, monitoring, and discharge. Patients with malignant pancreatic masses require cancer treatment (e.g., surgery). Those with potentially malignant pancreatic masses require surgery when they are invasive or high grade dysplasia, or monitoring otherwise. Those with non-malignant pancreatic masses may be safely discharged. Fine-grained classification of ten classes of pancreatic masses using multi-phase CT is difficult to achieve.

Existing automatic pancreatic mass image analysis methods focus on segmentation of certain types of tumors or cysts and thus cannot exploit full spectrum taxonomy of pancreatic masses/disease diagnoses. For the pancreatic disease diagnoses, both texture and geometry cues are clinically useful. For example, some types of pancreatic masses appear at specific locations of the pancreas. The AC and DC types appear only at a pancreas head while the MCN type rarely appears at the pancreas head. Other types spread over the entire pancreas, such as the CP and IPMN types. Additionally, some secondary signs of diseases are informative for diagnosis. Parenchymal atrophy and pseudocyst are observed in the CP type, causing a significant change in the shape of the pancreas. Most pancreatic cancers lead to dilation of the pancreatic duct, with the IPMN type in particular abruptly modifying its caliber.

In some embodiments, to integrate the above-described prior knowledge and/or correspondence into the machine learning model, a segmentation-based detection network is provided to segment and identify pancreatic disease regions simultaneously. The segmentation-based detection network takes multi-phase CT scans (e.g., 5-phase CT scan) as input and outputs segmentation masks of the pancreas (as the studied organ) and mass. In some embodiments, a weak-supervised segmentation method is provided for cases when all pixel-level PDAC annotations are available and only non-PDAC labels are available.

In some embodiments, a mask-to-mesh algorithm is provided to build a 3D correspondence-aware mesh from the pancreas segmentation output. The geometry of the pancreas together with the location, the shape, and the distributions of the detected mass are all captured and encoded by a mesh model. In some embodiments, a mesh-based feature pooling network that extracts features from the segmentation network and preserve the anatomic structure (each vertex of the mesh has its anatomic meaning) is provided. Based on a fixed vertex index list, the pancreas may be automatically divided or parsed into four zones (also known as regions, sections, or parts): pancreas head, ventral body, dorsal body, and pancreas tail.

In some embodiments, a geometry-integrated graph classification network is provided to utilize the 3D anatomy correspondence-aware mesh-based deep feature pooling to predict the pancreatic mass type. The geometry-integrated graph classification network includes graph-based residual convolutional blocks and an anatomy-based graph pooling layer.

The segmentation-based detection network, the mesh-based feature pooling network, and the geometry-integrated graph classification network are trained end-to-end via gradient-based optimization based on a loss function combining segmentation loss, mesh vertex classification loss, and global graph classification loss.

In the embodiments of the present disclosure, a multi-phase CT imaging analysis method for the full spectrum taxonomy of the pancreatic mass/disease diagnosis is provided. The 3D geometry-aware mesh model is integrated for effective pancreatic mass (tumor or cyst) imaging analysis, explicitly capturing the anatomy-mass integrated geometry and texture cues. The mesh model is evaluated on 661 patients (five-phase CT scans per patient) to achieve a PDAC segmentation accuracy with the dice score of 0.738. Compared with the baseline method nnUNet, the mesh model achieves a non-PDAC segmentation accuracy with the dice score of 0.611 versus the dice score of 0.478 for the baseline method and a detection accuracy with the detection rate of 89% versus the detection rate of 70% for the baseline method.

In the embodiments of the present disclosure, the imaging only automated approach demonstrates comparable performance levels with expert radiologists in the differentiation of PDAC versus non-PDAC when the expert radiologists combine the analysis on clinical factors, imaging, and blood tests, and a baseline clinical patient management system (i.e., surgery, monitoring, discharge) based on machine learning algorithm and using the multimodality tests.

Deep 3D reconstruction has been widely used in the computer vision and graphics fields and various methods may be used to learn 3D shapes of organs from medical images. A key component of mesh learning methods is the graph convolutional neural network (GCN), typically used for graph-structured data processing. For example, a liver mesh modeling method based on Vixel2Mesh algorithm simultaneously generates the mesh model and segmentation mask with improved geometry and segmentation accuracies. The Voxel2Mesh algorithm learns the mesh of the liver directly from 3D image volumes with a new mesh un-pooling operation for better mesh reconstruction. However, the method is designed specifically for organ segmentation but not for disease diagnosis.

When manual segmentations of masses are available, radiomics schemes are commonly used to classify disease types. However, heavy reliance on hand annotated masks makes radiomics models less reproducible and less scalable. In one example, a detection-by-segmentation network with U-Net as a common backbone network is used to achieve automation. In another example, nnU-Net (a self-adapting framework based on vanilla U-Nets) and its self-learning version achieve competitive accuracy on PDAC segmentation. In another example, shape-induced information (e.g., tubular structure of dilated duct) is used along with the PDAC segmentation task to improve disease diagnosis. These methods only work on PDAC or PNET and thus do not fully meet clinical needs on the full taxonomy of pancreatic tumor diagnosis. As such, the comprehensive taxonomy for pancreatic diseases is defined to help managing and treating patients where the machine learning models are built on top of clinical factors, imaging characteristics, and molecular biomarkers. However, these complex measurements require intensive labor costs and manual intervention, thereby reducing generalization and reproducibility.

Figure 2:
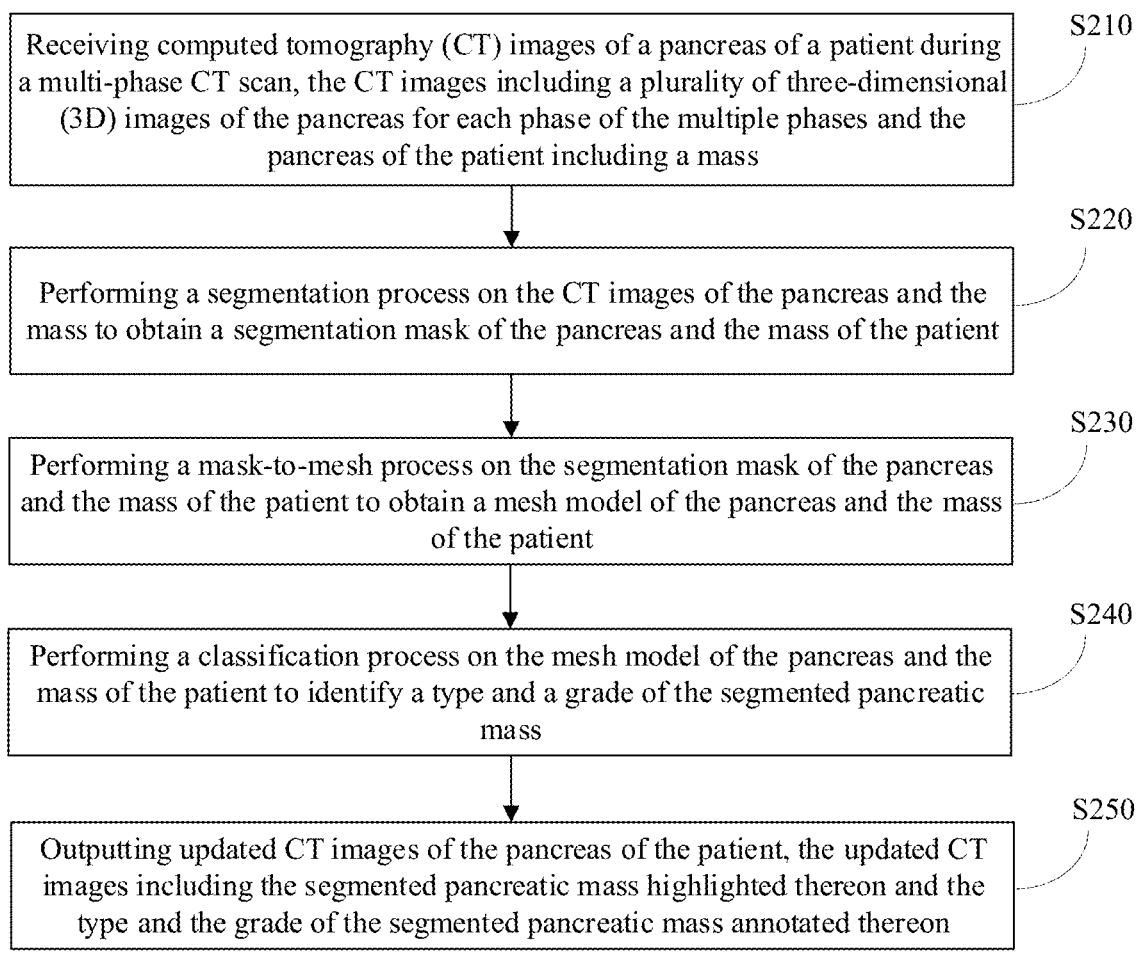
FIG. 2 illustrates a flowchart of an exemplary method for pancreatic mass diagnosis and patient management consistent with embodiments of the present disclosure.
Figure 3:
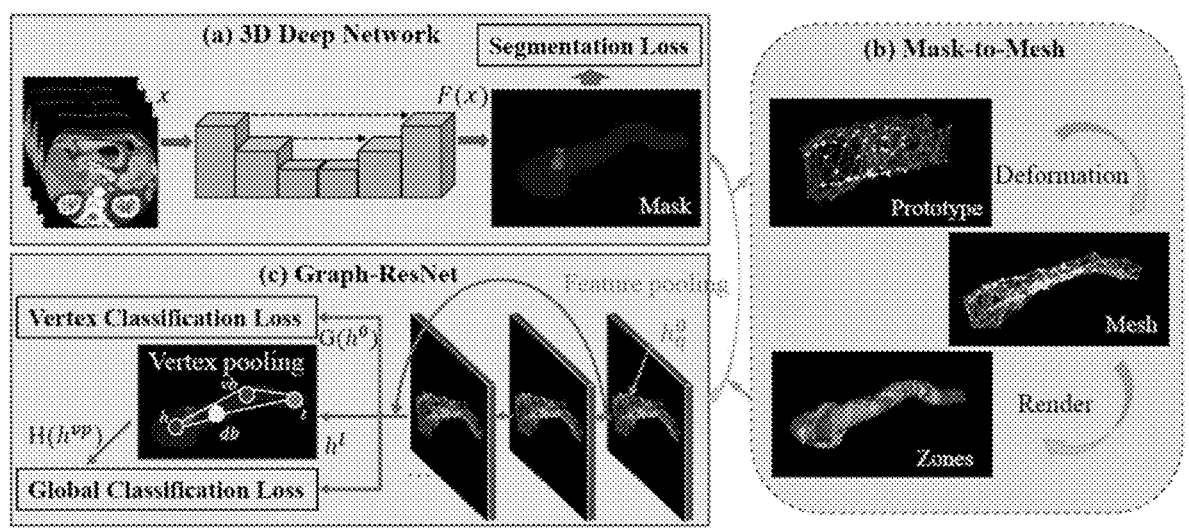
FIG. 3 illustrates an exemplary framework for pancreatic mass diagnosis and patient management consistent with embodiments of the present disclosure.

FIG. 2 illustrates a flowchart of an exemplary method for pancreatic mass diagnosis and patient management consistent with embodiments of the present disclosure. FIG. 3 illustrates an exemplary framework for pancreatic mass diagnosis and patient management consistent with embodiments of the present disclosure. As shown in FIG. 3, the framework includes a segmentation network, a mask-to-mesh modelling, and a global mass classification network. As shown in FIG. 2, the method includes receiving computed tomography (CT) images of a pancreas of a patient during a multi-phase CT scan, where the CT images includes a plurality of three-dimensional (3D) images of the pancreas for each phase of the multiple phases and the pancreas of the patient includes a mass (at S210). The pancreatic mass may be a tumor or a cyst. The tumor is a solid mass. The cyst is a liquid mass.

At S220, a segmentation process is performed on the CT images of the pancreas and the mass to obtain a segmentation mask of the pancreas and the mass of the patient.

Specifically, the plurality of multi-phase 3D CT images are concatenated into a 4D input X, where $X \in \mathbb{R}^{5 \times W \times H \times D}$ before being inputted into the segmentation network, R represents an image or a matrix, W is an image width, H is an image height, and D is an image depth (e.g., a number of slices in a CT volume). An input Y includes label/annotation for auto-segmented pancreas and radiologist-segmented PDAC and non-PDAC masses. The auto-segmented pancreases are segmented by an nnUNet model trained on a public pancreas dataset. The input Y is one-hot encoded and $Y \in \mathbb{R}^{K \times W \times H \times D}$. The numbers of labels K differ by tasks, such as PDAC vs non-PDAC or patient management. The segmentation network includes the nnUNet as the backbone network and a pixel level segmentation loss function $L_{seg}$. The loss function $L_{seg}$ combines cross-entropy $L_{CE}$ and dice $L_{DC}$ losses.

$$L_{CE} = -E_{w,h,d} \Sigma_k^K y_{k,w,h,d} \log(F(x)_{k,w,h,d}),$$

$$L_{DC} = -2 \sum_k^K \frac{\sum_{w,h,d} F(x)_{k,w,h,d} y_{k,w,h,d}}{\sum_{w,h,d} F(x)_{k,w,h,d} + \sum_{w,h,d} y_{k,w,h,d}}, \quad (1)$$

$$L_{seg} = L_{CE} + L_{DC},$$

where F(x) is a softmax output of the segmentation network, $F(x) \in R^{K \times W \times H \times D}$ and $y_{k,w,h,d}$ represents the k-th channel of F(x).

Non-PDAC labels are usually more difficult to obtain than PDAC labels due to their diversified appearance in a long-tail distribution. As such, the PDAC vs non-PDAC task is performed using only the PDAC mask annotations when the non-PDAC ones are unavailable. A segmentation model is trained on the PDAC data alone, focusing on PDAC segmentation. The PDAC data trained segmentation model is then applied to the non-PDAC data. A large portion of the non-PDAC masses are solid tumors that can be mistakenly detected as PDAC masses. All raw detections from the non-PDAC dataset by the PDAC data trained segmentation model are collected as pseudo non-PDAC labels. Then, a new segmentation network is trained by using both original PDAC labels and the pseudo non-PDAC labels.

Referring back to FIG. 2, at S230, a mask-to-mesh process is performed on the segmentation mask of the pancreas and the mass of the patient to obtain a mesh model of the pancreas and the mass of the patient.

Unlike existing mesh learning methods, that are initialized by a randomized ellipsoid mesh, the prior knowledge is encoded into an initial anatomy mesh by fitting it to the pancreas shape with anatomical meanings.

In one embodiment, a prototype mesh is created based on the average pancreas shape from a training fold. Then, 156 vertices that are equally distributed on a surface of the prototype mesh are placed to build an anatomic structure. In particular, the pancreas shape is separated into the four anatomical zones of the pancreas including the pancreas head, the ventral body, the dorsal body, and the pancreas tail. The first 48 vertices belong to the pancreas head. The $49^{th}$-$90^{th}$ vertices belong to the ventral body of the pancreas. The $90^{st}$-$135^{th}$ vertices correspond to the dorsal body of the pancreas. The last 21 vertices compose the pancreas tail.

Figure 4:
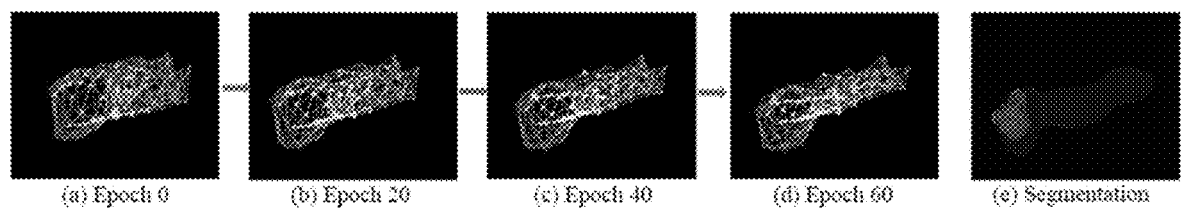
FIG. 4 illustrates an exemplary three-dimensional (3D) mesh deformation process consistent with embodiments of the present disclosure.

Further, the mesh is deformed to the segmentation mask of the pancreas of each patient as the target as shown in FIG. 4e. The geometry of the mesh can be deformed gradually to fit the surface of the segmentation mask, as shown in FIGS. 4a-4d, so as to preserve the true anatomy of the pancreas. In this way, the mesh maintains the anatomical meaning after deformation. To guide the deformation process, a loss function is defined to include a point loss term and two edge regularization terms. p is the vertex in the mesh and q is the voxels of the surface of the segmentation mask. The point loss term $L_{pt}$ measures a distance of each point to the nearest point at the surface of the segmentation mask.

$$L_{pt} = \sum_p \min_q \|p - q\|_2^2.$$

With the point loss term, the pancreas mesh is driven to fit the segmentation mask. Then, a first edge regularization term $L_{e1}$ is provided to preserve the geometry of the mesh. $L_{e1} = \Sigma_e \|e - \text{mean}(e)\|_2^2$, $e = \|p - p'\|_2$, $p' \in N(p)$, and N(p) is neighboring vertices of the vertex p. To penalize the flying vertices (i.e., abnormal vertices randomly updated during the deformation process, resulting in structure flaws), a second edge regularization term $L_{e2}$ is provided to simply minimize the edge length. $L_{e2} = \Sigma_e e$. The overall loss function $L_{meshfit}$ is $$L_{meshfit} = L_{pt} + \lambda_1 L_{e1} + \lambda_2 L_{e2}, \quad (2)$$

where, $\lambda_1 = 10^{-4}$, and $\lambda_2 = 10^{-2}$.

It should be noted that the mesh vertices keep their anatomic meanings even after the deformation process is completed. The mesh fitting process automatically parses the pancreas head, the ventral body, the dorsal body, and the pancreas tail and preserves the anatomy-aware information in the mesh deformation process.

The pancreas is divided into zones Z(p) based on the coordinates of the mesh vertices. Each voxel of the segmented pancreas volume is defined in a zone by its nearest vertex, as shown in FIG. 3b. The rendering method to define the zones from each vertex includes the following processes. The vertex in a 3D volume A is labeled by its index, that is, the ith vertex at (w,h,d) is labeled as i, where $A \in R^{W,H,D}$, and $A_{w,h,d} = i$. All the other voxels of A are set to zero. The 3D volume A is dilated by one voxel as A'. Each zero voxel in A with a corresponding non-zero voxel in A' that belongs to the pancreas in the segmentation output F(x) is substituted with the corresponding voxel in A'. The dilation and substitution processes are repeated until all voxels have been updated.

Referring back to FIG. 2, at S240, a classification process is performed on the mesh model of the pancreas and the mass of the patient to identify a type and a grade of a segmented pancreatic mass.

In some embodiments, a deformed mesh and its representative vertex zones are integrated into a deep network for shape-constrained detection and segmentation. The anatomical structure of the pancreas as well as the tumor's texture and geometry are encoded into a feature vector. As such, the feature vector is viewed as an anatomical representation of the pancreas and tumor of interest. $h_p^0$ is defined as the initialized feature vector attached to a vertex p of the pancreas mesh, as shown in FIG. 5a and FIG. 5c. The anatomical feature representation includes vertex coordinates $(x_p, y_p, z_p)$, an average edge length to its neighbors $e_p$, a distance from the vertex p to the nearest tumor surface point $d_p$, and the local and global feature vectors pooled from prediction probability maps of the segmentation network. More specifically, $$e_p = \sum_{p' \in N(p)} e_{pp'} / |N(p)|,$$

$$d_p = \min_r \|p - r\|_2^2,$$

$$p' \in N(p),$$

$N_{(p)}$ is neighboring vertices of the vertex p, and r is a tumor/cyst surface point (as shown in FIG. 5e). The zone Z(p) then acts as a receptive field within which the prediction probability maps of the 3D segmentation network F(x) are pooled to obtain a local feature vector, as shown in FIG. 5b. The prediction probability maps within the receptive field is represented as a list of feature vectors $F(x)_{w,h,d} \in R^K$, where $(w,h,d) \in Z(p)$, and K is a label indicating a task, such as a PDAC vs non-PDAC classification task or a treatment recommendation task.

In addition to mesh-based feature pooling, a global average pooling is performed to obtain a global feature vector from the prediction probability maps of the 3D segmentation network in FIG. 5b. The meta information, the local feature vectors of each individual vertex, and the global feature vector of the entire mesh are concatenated to form the initialized feature vector $h_p^0$ for each vertex p. The pancreas-to-tumor geometry, the tumor's location in the pancreas, and its texture in the mesh-based anatomy representation are explicitly encoded in the feature vector. This approach improves the segmentation model's ability to learn anatomy-aware features, and improves the performance in pancreatic mass/disease diagnosis based on the full spectrum pancreatic disease taxonomy.

In some embodiments, after the feature vectors $h_i$ are obtained for each vertex p, the feature vectors $h_i$ are fed into the graph-based residual convolutional network (Graph-ResNet). In some other embodiments, other neural network may replace the Graph-ResNet. The original Graph-ResNet is reduced to a smaller network including six graph convolutional layers and shortcut connections between every two layers to perform the mass classification task under three granularity levels including pixel, vertex, and global levels. Each graph-based convolutional layer is defined as:

$$h_p^{l+1} = w_0 h_p^l + \Sigma_{p' \in N(p)} w_1 h_{p'}^l, \quad (3)$$

where $h_p^l$ is the feature vector attached to the vertex p at layer l of the Graph-ResNet, and $w_0$ and $w_1$ are learned parameters with $w_1$ being shared by all edges.

The graph-based convolutional layer accounts for the way in which vertices neighboring a given vertex regularize the vertex-to-neighbor exchange of information. Two classification training losses are used: a vertex level classification loss and a global classification loss. The vertex level classification loss is defined as a cross-entropy loss and is applied to each vertex as $$L_{vertex} = -\Sigma_p \Sigma_k^K y_{k,p}^v \log(G(h^0)_{k,p}), \quad (4)$$

where $G(h^0)$ is a softmax output of the Graph-ResNet at every vertex, a vertex label $y^v$ is a one hot encoding of $\hat{y}_p^v$ inferred from a labeled mask, background voxels are labeled as 0, pancreas voxels are labeled as 1, voxels for tumor mass types are labeled with a number greater than 1, the vertex p is labeled using the maximum value of the voxels in its corresponding zone Z(p), and $$\hat{y}_p^v = \max_{(w,h,d) \in Z(p)} \hat{y}_{w,h,d}.$$

Considering that some mass types have blurry boundaries and the mass neighbor may also contain relevant cancer-related information, the labeling strategy and the propagation/smoothing property of the Graph-ResNet makes the approach robust to the quality of the segmentation annotations or labels and improves the detection rates of the pancreatic masses.

After being processed by the Graph-ResNet, four features from all four pancreatic regions or zones are pooled according to the vertex indices (1-48, 49-93, 94-135, and 136-156), as shown in FIG. 3. The four global feature vectors and 156 local feature vectors are concatenated into one combined feature vector $h^{vp}$ and are fed into the final mass classification layer. The final global classification layer is a fully connected layer. The global classification loss is the cross-entropy loss:

$$L_{global} = -\Sigma_k^K y_k^g \log(H(h^{vp})_k), \quad (5)$$

where $H(h^{vp})$ is a softmax output of the fully connected global classification layer, and $y^g$ is a patient level mass/disease label.

The overall loss function is the combination of three losses:

$$L = L_{seg} + \eta_1 L_{vertex} + \eta_2 L_{global}, \quad (6)$$

where $\eta$ is a hyperparameter used to balance the three loss components, $L_{seg}$ is the pixel-level segmentation loss, and $L_{vertex}$ is the vertex classification loss. All networks (the 3D segmentation network and the classification Graph-ResNet) are trained end-to-end by leveraging this combined loss function.

Referring back to FIG. 2, at S250, updated CT images of the pancreas of the patient are outputted, where the updated CT images include the segmented pancreatic mass highlighted thereon and the type and the grade of the segmented pancreatic mass annotated thereon.

Specifically, the voxels associated with the tumor/cyst are marked on the plurality of multi-phase 3D CT images. In some embodiments, only the 3D CT images of one of the five phases are annotated to illustrate the tumor/cyst geometry along with the type of the tumor/cyst. Further, the treatment recommendation is provided for the patient management. Outputting the plurality of multi-phase 3D CT images may include displaying the plurality of multi-phase 3D CT images on a screen, printing the one or more images by a printer, transmitting the plurality of multi-phase 3D CT images to a remote device via a communication network, or storing the plurality of multi-phase 3D CT images in a storage device for future viewing.

The disclose method is evaluated using a dataset including 661 patients with surgical pathology-confirmed pancreatic masses. Specifically, the dataset includes 366 PDACs, 46 ACs, 12 DCs, 35 PNETs, 13 RAREs, 32 SPTs, 43 CPs, 61 IPMNs, 7 MCNs, and 46 SCNs. Each patient has 5-phase CT scans including non-contrast (NC), arterial-early ($\Delta$E), arterial-late (AL), venous (V), and delay (D). The median voxel size is 0.419×0.419×3 mm³. The manual annotations of pancreatic masses were performed by an experienced pancreatic imaging radiologist on the AL phase. The CT scans from the other four phases are registered to the AL phase by DEEDS. Data augmentation is performed on-the-fly. This includes spatial transforms, Gaussian blur, and contrast shifting. The hyper-parameters are set as $\lambda_1 = 10^{-4}$, $\lambda_2 = 10^{-2}$, and $\eta_1 = \eta_2 = 0.1$ based on evaluation results. All evaluation processes are performed using nested three-fold cross-validation. In each fold, the neural networks are trained for 1,000 epochs. The best model is selected based on the performance on a validation dataset, and is then applied to the test dataset to generate the final evaluation results.

The evaluation process on the mass segmentation includes a quantitative evaluation process and a qualitative evaluation process. Segmentation accuracy is measured using the dice coefficient. Dice scores and detection rates of the PDACs and non-PDACs (10 diseases in total) are provided in Table 1 below. The neural networks are trained with four labels: background, pancreas, PDAC, and non-PDAC. The micro column shows results for all patients. The macro column shows an average of the metrics of the ten classes. SMCN stands for segmentation, mesh, and classification network consistent with the embodiments of the present disclosure. nnUNet refers to the baseline network with which the evaluation results of SMCN are compared. Ave. dice refers to the average dice score and Det. Rate refers to the detection rate.

TABLE 1

| | Metric | PDAC | Non-PDAC | AC | CP | DC | IPMN | MCN | PNET | RARE | SCN | SPT | micro | macro |
|---|---|---|---|---|---|---|---|---|---|---|---|---|---|---|
| nnUNet | Ave. dice | 0.734 | 0.478 | 0.423 | 0.533 | 0.001 | 0.151 | 0.924 | 0.514 | 0.849 | 0.585 | 0.762 | 0.618 | 0.548 |
| | Det. rate | 0.959 | 0.693 | 0.700 | 0.778 | 0.000 | 0.308 | 1.000 | 0.833 | 1.000 | 0.800 | 1.000 | 0.838 | 0.738 |
| SMCN | Ave. dice | 0.738 | 0.611 | 0.438 | 0.668 | 0.006 | 0.602 | 0.924 | 0.514 | 0.824 | 0.666 | 0.801 | 0.681 | 0.618 |
| | Det. rate | 0.972 | 0.887 | 0.800 | 0.889 | 0.000 | 1.000 | 1.000 | 1.000 | 1.000 | 0.800 | 1.000 | 0.934 | 0.846 |

A detection is considered successful if the intersection (between the ground truth and segmentation mask) over the ground truth is >10% (counted as 1). Otherwise, it is considered a misdetection (counted as 0). The SMCN network is compared with the baseline network (3D nnUNet), which is trained from scratch on the same dataset as the SMCN network. It is observed that integrating the 3D mesh-based anatomy representation into Graph-ResNet substantially improves mass segmentation and detection accuracies relative to the baseline nnUNet's, especially for non-PDACs. For example, the dice score of the SMCN network is 0.611 while the dice score of the nnUNet is 0.478. The detection rate of the SMCN network is 88.7% while the detection rate of the nnUNet is 69.3%.

Figure 6:
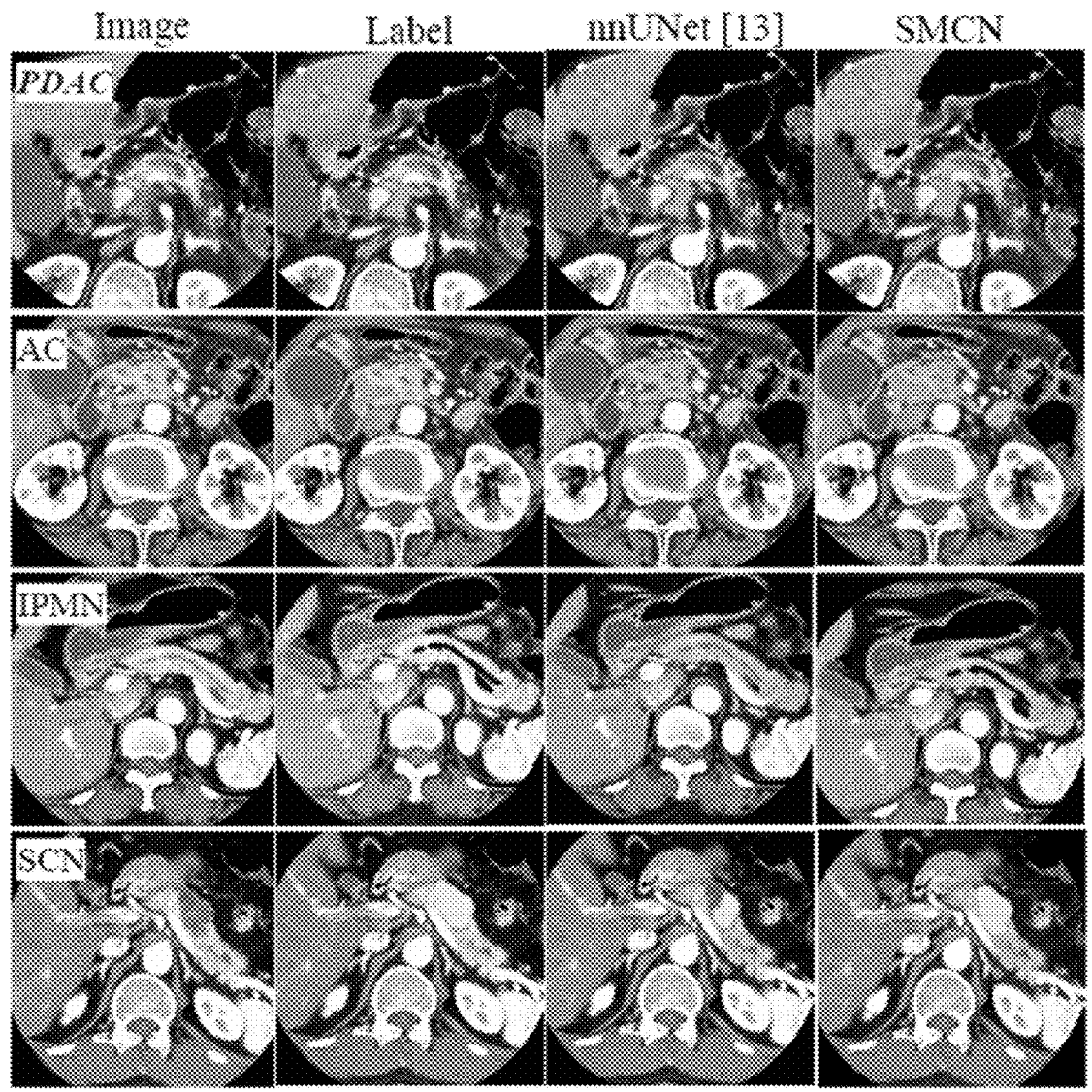
FIG. 6 illustrates exemplary pancreatic mass segmentation results consistent with embodiments of the present disclosure.

FIG. 6 illustrates exemplary pancreatic mass segmentation results consistent with embodiments of the present disclosure. The SMCN model guides the segmentation network by integrating geometry cues and achieves more complete segmentation results, especially for harder and relatively rare non-PDAC classes. In one example, as shown in FIG. 6, the nnUNet model mis-detects an AC (malignant) completely because the tumor is outside of the pancreas head. The SMCN model instead detects the same AC. In another example, for an IPMN (malignant potential), the SMCN model provides more complete segmentation including the clinically-critical secondary signs of pancreatic duct dilation than the nnUNet model. In another example, for an SCN (benign), the SMCN model segments the full tumor surface. FIG. 6 demonstrates that the anatomy-aware SMCN network produces better segmentation results than the baseline nnUNet network, which is widely used in medical imaging applications.

Further, the SMCN model is compared with three other methods which are applied to the venous phase. For the purpose of comparison, the SMCN model is evaluated using one or a few CT phases as shown in Table 2 below.

TABLE 2

| Methods | CT phases | Average dice score |
|---|---|---|
| Method 1 | NC + A + V | 0.709 |
| Method 2 | V | 0.634 |
| Method 3 | A + V | 0.644 |
| SMCN | AE | 0.646 |
| SMCN | AL | 0.730 |
| SMCN | V | 0.675 |
| SMCN | D | 0.562 |
| SMCN | NC + AE + V + D | 0.696 |
| SMCN | NC + AE + AL + V + D | 0.738 |

The AL phase outperforms all other individual phases due to its higher voxel resolution and imaging contrast. The second best is the V phase, which is widely adopted in clinical settings. The fusion/concentration of multiple CT phases as inputs to the SMCN network yields better results than any individual phase alone. The combined five phases yield the best segmentation dice score of 0.738, which noticeably improves upon the existing state-of-the-art result of 0.709. It was assumed that PDACs are mostly small in size and are only located at the pancreas head. In the actual dataset available, by contrast, PDACs appear in various sizes and span the entire pancreas. The fusion of all four phases but the AL phase as the inputs yields better results than any individual phase alone as well. For example, the dice score of the SMCN model is 0.696 versus the dice score of the other methods ranging between 0.562 and 0.675.

Figure 7:
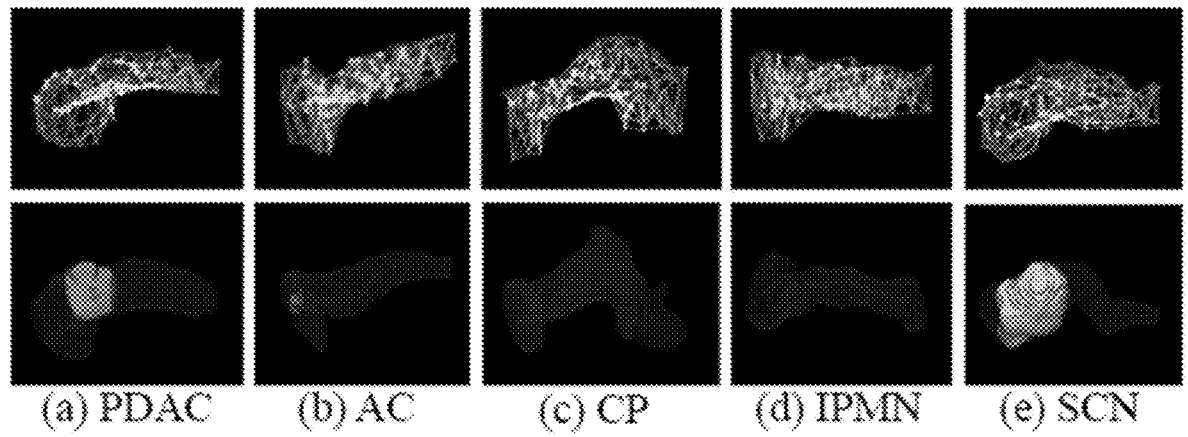
FIG. 7 illustrates exemplary 3D meshes generated from pancreas segmentation consistent with embodiments of the present disclosure.

FIG. 7 illustrates exemplary 3D meshes generated from pancreas segmentation consistent with embodiments of the present disclosure. As shown in FIG. 7, the SMCN network effectively and accurately models the diseased pancreas under various scenarios. For example, PDAC at the neck (FIG. 7a), AC at the head with pancreatic duct dilation (FIG. 7b), pseudocyst at the tail (FIG. 7c), IPMN on the full pancreatic duct (FIG. 7d), and large tumor and parenchymal atrophy (FIG. 7e). In the embodiments of the present disclosure, the mask-to-mesh algorithm automatically divides the pancreas into four parts or zones: pancreas head, ventral body, dorsal body, and pancreas tail.

The distributions of anatomic locations of 10 classes or types of the pancreatic masses in the dataset available are described further later in the specification. AC and DC only appear at the pancreas head. MCN does not appear at the pancreas head. CP and IPMN appear mostly at the pancreas head. PDAC, PNET, and RARE are distributed over the entire surface of the pancreas. Cystic masses (SPT, SCN, and MCN) are distributed over the entire pancreas with the majority being located at the dorsal body. The observed distributions verify the prior knowledge of different masses' spatial locations and motivate the geometry-aware mass diagnosis framework.

Figure 5:
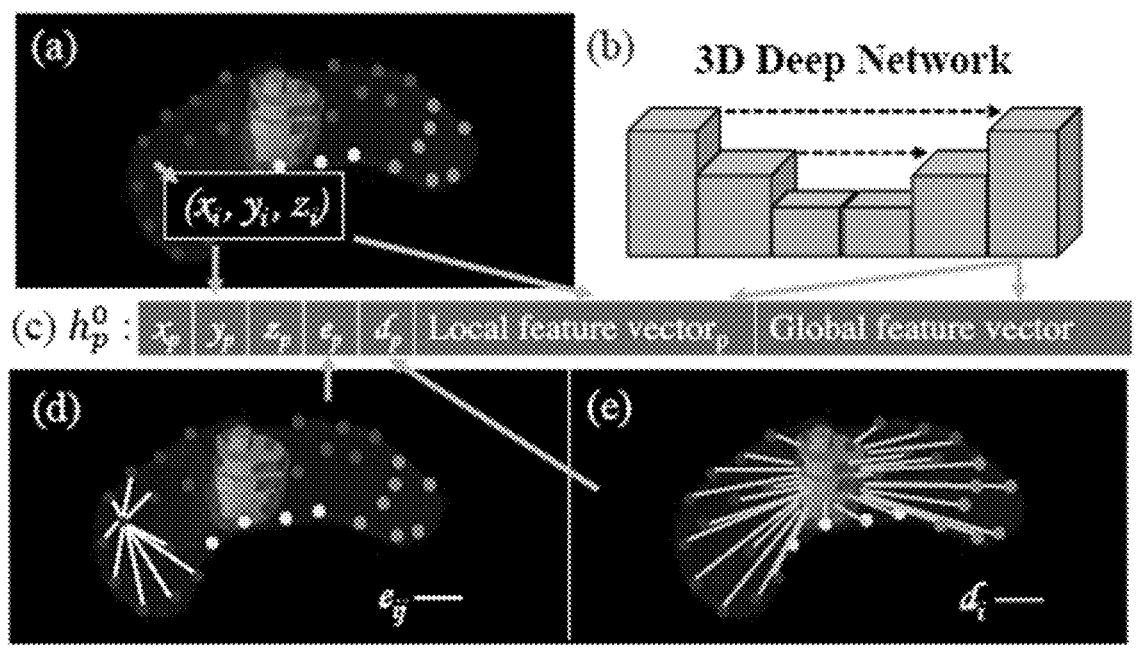
FIG. 5 illustrates schematic diagrams of a feature vector $h_i$ for an ith vertex consistent with embodiments of the present disclosure.

From the generated 3D nesh model, the shape and location of the mass against the pancreas are accurately measured, as shown in FIG. 5, at a human-readable level. 156 vertices are a suitable number for the clinical expert's perception. The mask-to-mesh algorithm and the SMCN models may be generalized to other important organs such as a liver with specific anatomical structures, which may improve the underlying imaging-based mass diagnosis.

The SMCN model has been validated for two mass classification tasks: PDAC vs non-PDAC and patient management. The SMCN model is compared with the radiomics model and 2D/3D deep classification networks. Pyradiomics package is used to extract 2,410 radiomics features (482 features per each CT phase) from the manually-annotated masses. The features include mass characteristics of various-ordered texture and shape descriptions. Gradient boosting decision tree is used as the classifier. Feature importance is calculated within each phase to select the most informative features (top 30) in the training fold. To compare with other deep classification models, automatic mass segmentation is used to prepare 2D/3D tumor patches/volumes from all five phases. Each 2D patch is the tumor region representing the largest size in the axial view of the 3D volume which is then resized to 256×256 following typical texture analysis practices. For 3D volumes, ResNet3D is used in the testing while for 2D patches, deep texture networks are built using ResNet-18 as the backbone network, following the model.

Classifying PDAC versus non-PDAC is the primary clinical diagnosis task. The SMCN model is compared with three other methods with comparison results shown in Table 3 below.

TABLE 3

| Methods | Accuracy | Sensitivity | Specificity |
|---|---|---|---|
| Radiomics | 0.857 | 0.853 | 0.868 |
| DeepTexture | 0.770 | 0.827 | 0.697 |
| ResNet3D | 0.720 | 0.788 | 0.633 |
| SMCN with PV | 0.913 | 0.945 | 0.875 |
| SMCN with VV | 0.920 | 0.945 | 0.891 |
| SMCN with GC | 0.927 | 0.945 | 0.906 |
| Expert radiologist | — | ~0.94 | ~0.90 |

Sensitivity and specificity correspond to the proportions of correctly predicted PDACs and non-PDACs, respectively. Table 3 shows several classification strategies. Pixel voting (PV) indicates that the classification result is voted by the pixels from the segmentation masks, that is, using an optimal volume threshold from the validation dataset. Vertex voting (VV) indicates that the classification result is voted by the classified vertices of Graph-ResNet. Global classification (GC) refers to the embodiments of the present disclosure. All SMCN variations significantly outperform the 2D/3D deep networks, thereby revealing that using only the tumor's texture information to distinguish PDAC from non-PDAC is insufficient. The fully automated models consistent with the present disclosure outperform the radiomics approach using the manual annotations. The SMCN with GC configuration reports the best quantitative results with a sensitivity of 0.945 and a specificity of 0.906, which are no worse than the expert radiologist.

Figure 8:
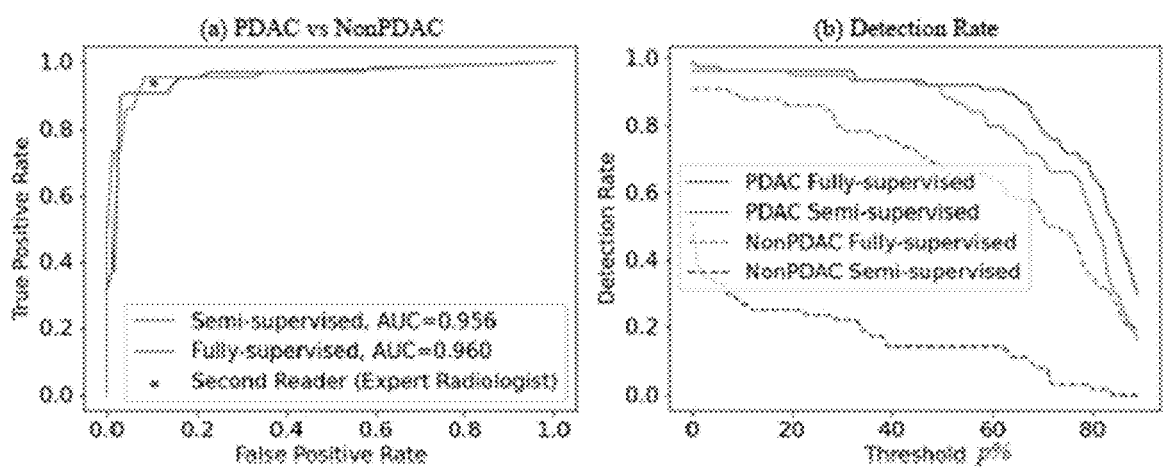
FIG. 8 illustrates comparison of fully-supervised and semi-supervised learning for classification and detection consistent with embodiments of the present disclosure.

As described previously, PDAC versus non-PDAC task may be performed even when only the patient level non-PDAC labels are available (referred as semi-supervised). A fully supervised setting means that both PDAC and non-PDAC annotated masks can be obtained. Receiver operating characteristic (ROC) curves of PDAC (positive class) versus non-PDAC (negative class) are shown in FIG. 8a. Generally, similar classification results are achieved by the fully supervised or semi supervised learning method. Using only pseudo non-PDAC masks in a semi supervised setting slightly reduces the detection rate of PDAC. The fully supervised method obtains the sensitivity and specificity comparable to the mean second reader at a high-volume pancreatic cancer institution at 94% and 90%, respectively. The detection rates by different thresholds are evaluated in FIG. 8b. A segmentation result is counted as successful detection if at least the fraction f of the mass is segmented (f is the cut-off). For fully supervised learning, the best PDAC detection rate is 0.986 (f>0). The best non-PDAC sensitivity is 0.906 (f≅0.08). Under semi supervised learning, the numbers are 0.959 (f≅0.2) and 0.515 (f>0), revealing the limitation of semi supervised setting.

In some embodiments, patient management decisions or treatment recommendations fall under three categories: surgery, monitoring, and discharge (FIG. 1). In some other embodiments, the treatment recommendations may include immediate treatment, monitoring, and being discharged. The immediate treatment may include the surgery or another form of medical treatment, which is not limited by the present disclosure. The disclosed method is compared with the baseline radiomics, which is the current clinical standard approach. Results under different classification strategies: PV, VV, and GC are shown in Table 4 below.

TABLE 4

| Methods | Accuracy | Average recall |
|---|---|---|
| Radiomics | 0.854 | 0.667 |
| DeepTexture | 0.743 | 0.557 |
| ResNet3D | 0.737 | 0.607 |
| SMCN with PV | 0.832 | 0.735 |
| SMCN with VV | 0.839 | 0.656 |
| SMCN with GC | 0.865 | 0.746 |

The SMCN method outperforms the radiomics method. The SMCN with GC configuration yields the best results. Generally, the pancreatic mass patient management decisions leverage clinical features, imaging characteristics, cyst fluid genetic and biochemical markers. However, the approach is invasive, more expensive, and more time consuming than the SMCN method. For the purpose of comparison, the pancreatic disease taxonomy excludes AC, DC, and RARE classes. Two confusion matrices and the SMCN are compared side-by-side in Table 5 below. The baseline method data are obtained from CompCyst.

TABLE 5

| Baseline method | Discharge | Monitoring | Surgery | SMCN method | Discharge | Monitoring | Surgery |
|---|---|---|---|---|---|---|---|
| Discharge (n = 53) | 32(60%) | 14(26%) | 7(13%) | (n = 46) | 28(61%) | 10(22%) | 8(17%) |
| Monitor (n = 140) | 1(1%) | 68(49%) | 71(51%) | (n = 104) | 11(11%) | 65(63%) | 27(26%) |
| Surgery (n = 152) | 0(0%) | 14(9%) | 138(91%) | (n = 440) | 6(1%) | 16(4%) | 418(95%) |

The SMCN method achieves similar or slightly improved quantitative performance via multi-phase CT imaging. Compared with 91% for the baseline method, 95% of surgery patients are correctly guided to surgery while 1% of the surgery patients are misclassified as discharge patients. The correctly recommended monitoring patients increase to 63% for the SMCN method from 49% for the baseline method. The error rate for recommending surgery decreases from 51% for the baseline method to 26% for the SMCN method. The performance for discharge patients is similar between the SMCN method and the baseline method. More patients (17% for the SMCN method versus 13% for the baseline method) are classified into the surgery class due to the fact that the distribution of the patients among all three actionable classes is less even in the evaluation dataset for the SMCN method which includes a insufficient number of patients in the discharge class.

In the embodiments of the present disclosure, a segmentation, mesh, and classification deep network (SMCN) is provided to tackle the challenging and clinically demanding tasks of pancreatic mass segmentation, diagnosis, and patient management. The SMCN includes am anatomy-aware segmentation network, a mask-to-mesh 3D geometry modeling network, and a Graph-ResNet with vertex feature pooling and may be trained end-to-end. The SMCN method is evaluated using a large pancreatic multi-phase CT image dataset of 661 patients to cover the full taxonomy of ten types of pancreatic masses, and the evaluation results demonstrate desirable performances for the pancreatic mass segmentation, diagnosis, and patient management.

The inputs of the SMCN model are 5-phase 3D CT images for each patient: non-contrast, arterial-early, arterial-late, venous, and delay phases, ordered by the acquisition time during the CT imaging process. The non-contrast phase is generated with less contrast. Then the intravenous-injected contrast media is gradually applied or supplied into human body to increase the visibility of blood vessels (i.e., hyper-intensity patterns). In the arterial-early phase, the arterial vessels become bright. In the arterial-late phase, the pancreas has a properly high imaging contrast which makes it the most suitable phase to observe the mass and perform diagnosis. In the venous phase, the venous vessels become bright in turn. Finally, in the delay phase, the brightness in all blood vessels vanishes and the kidneys become bright. Only the arterial-late phase has a high resolution on the transverse plane (median spacing is 0.419×0.419×3 mm$^3$ in [X, Y, Z]). The other four phases have a relatively lower resolution on the transverse plane (median spacing is 0.682× 0.682×3 mm$^3$). CT scans from the other four phases are spatially registered to the arterial-late phase. The input image size for inference is at the scale of 5×512×512×54 voxels.

The SMCN can guide the pancreas-mass segmentation network by integrating geometry cues and achieve more complete segmentation results, especially for harder and relatively rare non-PDAC classes. The SMCN model can detect both small masses as in the DC and PNET cases, and large masses as in the SPT and MCN cases. In AC case, the SMCN model can detect the tumor which is outside of the pancreas head. In PNET and IPMN scenarios, the SMCN model detects (by segmentation) both the mass and the dilated duct. In the IPMN-high case, the SMCN model labels both the low grade IPMN mass and the high grade IPMN mass successfully. All example, collectively demonstrate that the graph-based anatomy geometry-aware SMCN network produces superior segmentation results.

The 3D mask-to-mesh algorithm can automatically divide the segmented pancreas into four anatomical regions or sub-regions of the pancreas: pancreas head, ventral body, dorsal body, and pancreas tail. AC and DC only appear at the head. MCN does not appear at the head. CP and IPMN appear mostly at the head. PDAC, PNET, and RARE are distributed over the entire surface of the pancreas. Cystic masses (SPT, SCN, and MCN) are distributed over the entire pancreas with majority being located at the dorsal body. These observed distributions verify the prior knowledge of different masses' spatial locations and motivate the geometry-aware mass diagnosis framework.

The patient level 10-class pancreatic mass classification results are provided in Table 6 below.

ance of DC is very confusing against PDAC and occurs statistically rarely. RARE labeled patients often have multiple co-existing diseases, which makes the diagnosis more difficult. Precisely classifying the ten pancreatic tumor classes is a difficult long-tail disease recognition and reasoning problem though it is also clinically less critical.

Figure 9:
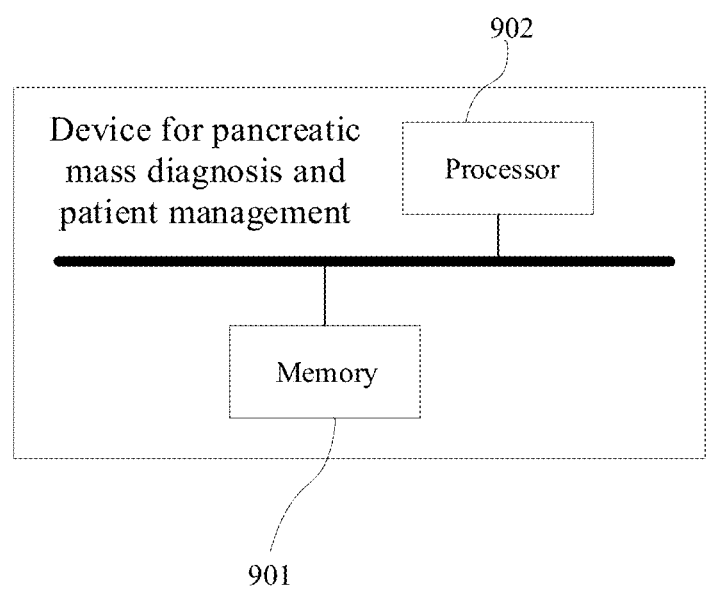
FIG. 9 illustrates a structural diagram of an exemplary device for pancreatic mass diagnosis and patient management consistent with embodiments of the present disclosure.

FIG. 9 illustrates a structural diagram of an exemplary device for segmentation, mesh, and classification consistent with embodiments of the present disclosure. Referring to FIG. 9, the present disclosure provides a device for pancreatic mass diagnosis and patient management. The device performs the disclosed method for pancreatic mass diagnosis and patient management. Specifically, the device includes a memory 901 storing a computer program and a processor 902 configured to execute the computer program stored in the memory 901 to: receive computed tomography (CT) images of a pancreas of a patient during a multi-phase CT scan, the CT images including a plurality of three-dimensional (3D) images of the pancreas for each phase of the multiple phases and the pancreas of the patient including a mass; perform a segmentation process on the CT images of the pancreas and the mass to obtain a segmentation mask of the pancreas and the mass of the patient; perform a mask-to-mesh process on the segmentation mask of the pancreas and the mass of the patient to obtain a mesh model of the pancreas and the mass of the patient; perform a classification process on the mesh model of the pancreas and the mass of the patient to identify a type and a grade of the segmented pancreatic mass; and output updated CT images of the pancreas of the patient, the updated CT images including the segmented pancreatic mass highlighted thereon and the type and the grade of the segmented pancreatic mass annotated thereon.

In some embodiments, the processor 902 is further configured to provide a treatment recommendation, based on a degree of malignancy of the segmented pancreatic mass. The type of the segmented pancreatic mass includes pancreatic ductal adenocarcinoma (PDAC), ampullary cancer (AC), bile duct cancer (DC), pancreatic neuroendocrine tumor (PNET), rare neo-plasma (RARE), solid pseudopapillary tumor (SPT), chronic pancreatitis (CP), intraductal papillary mucinous neoplasm (IPMN), mucinous cystic neoplasm (MCN), and serous cystic neoplasm (SCN). The grade of the segmented pancreatic mass includes a low grade, an intermediate grade, and a high grade. PDAC, AC, DC, PNET, RARE, and SPT are malignant types, CP, IPMN, and MCN are potentially malignant types, and SCN is a non-malignant type. The patient with the malignant types and the potentially malignant types with the high grade need immediate treatment, the patient with the potentially malignant types with the low and intermediate grades need monitoring, and the patient with the non-malignant type is discharged.

In some embodiments, the processor 902 is further configured to concatenate the CT images of the pancreas of the

TABLE 6

| Class | PDAC | AC | CP | DC | IPMN | MCN | PNET | RARE | SCN | SPT | Ave. |
|---|---|---|---|---|---|---|---|---|---|---|---|
| Recall | 0.949 | 0.488 | 0.473 | 0 | 0.759 | 0.333 | 0.330 | 0 | 0.533 | 0.420 | 0.428 |
| Precision | 0.904 | 0.623 | 0.663 | — | 0.427 | 0.167 | 0.426 | — | 0.515 | 0.733 | 0.557 |

Dominant tumor types achieve good accuracies (e.g., PDAC, IPMN, SPT), but others have relatively low performance, especially for DC and RARE. The imaging appear-patient to form a four-dimensional (4D) input X, where $X \in \mathbb{R}^{N \times W \times H \times D}$, where the multi-phase CT scan is an N-phase CT scan, and N is a positive integer.

In some embodiments, when performing the segmentation process on the CT images of the pancreas and the mass to obtain the segmentation mask of the pancreas and the mass, the processor 902 is configured to feed the 4D input X into a segmentation network trained on an input Y which is one-hot encoded by combining a public pancreas dataset with masses of radiologist-segmented pancreatic ductal adenocarcinoma (PDAC) and radiologist-segmented non-PDAC, to obtain the segmentation mask of the pancreas. $Y \in R^{K \times W \times H \times D}$, K is a task label indicating a task including a classification task between the masses of the PDAC and the non-PDAC (e.g., K=2), and a treatment recommendation task (e.g., K=3), the segmentation network includes an nnUNet as a backbone network and a pixel-level segmentation loss function $L_{seg}$ $$L_{seg} = -\sum_{w,h,d} \sum_k^K y_{k,w,h,d} \log(F(x)_{k,w,h,d}) - 2\sum_k^K \frac{\sum_{w,h,d} F(x)_{k,w,h,d} y_{k,w,h,d}}{\sum_{w,h,d} F(x)_{k,w,h,d} + \sum_{w,h,d} y_{k,w,h,d}},$$

F(x) is a softmax output of the nnUNet, and $F(x) \in R^{K \times W \times H \times D}$.

In some embodiments, when performing the mask-to-mesh process on the segmentation mask of the pancreas and the mass of the patient to obtain the mesh model of the pancreas and the mass of the patient, the processor 902 is configured to: obtain the initial mesh model including 156 vertices of an average pancreas; gradually deform the initial mesh model to fit a surface of the segmentation mask of the pancreas and the mass of the patient to preserve an anatomy of the pancreas of the patient; and render the deformed mesh model to include the 156 vertices distributed in four zones of the pancreas of the patient.

In some embodiments, when obtaining the initial mesh model including the 156 vertices of the average pancreas, the processor 902 is configured to: obtain a prototype mesh model based on an average pancreas shape from a training dataset; and place 156 vertices equally distributed on a surface of the prototype mesh model to build an anatomic structure including the four zones: a pancreas head, a ventral body, a dorsal body, and a pancreas tail. The pancreas head includes the $1^{st}$-$48^{th}$ vertices, the ventral body includes the $49^{th}$-$90^{th}$ vertices, the dorsal body includes the $90^{th}$-$135^{th}$ vertices, and the pancreas tail includes the $136^{th}$-$156^{th}$ vertices.

In some embodiments, when gradually deforming the initial mesh model to fit the surface of the segmentation mask of the pancreas and the mass of the patient to preserve the anatomy of the pancreas of the patient, the processor 902 is configured to guide the deformation process by a loss function $L_{meshfit}$ $$L_{meshfit} = \sum_p \min_q \|p - q\|_2^2 + \lambda_1 \sum_e \|e - \text{mean}(e)\|_2^2 + \lambda_2 \sum_e e,$$

p is a vertex in the mesh model, q is a voxel of the surface of the segmentation mask of the pancreas, $\lambda_1 = 10^{-4}$, $\lambda_2 = 10^{-2}$, $e = \|p - p'\|_2$, $p' \in N(p)$, and N(p) are neighboring vertices of the vertex p.

In some embodiments, when rendering the deformed mesh model to include the 156 vertices distributed in the four zones of the pancreas of the patient, the processor 902 is configured to: divide the deformed mesh model of the pancreas and the mass of the patient into the four zones Z(p) based on coordinates of vertices of the deformed mesh model, where p is a vertex in the deformed mesh model; label a vertex at a coordinate (w,h,d) in a 3D volume A by an index i and a voxel corresponding to the vertex as $A_{w,h,d}$, and set all other voxels of A to 0, where $A \in R^{W,H,D}$, and $A_{w,h,d} = i$; dilate A by one voxel as A' and substituting each zero voxel in A with a corresponding non-zero voxel in A' that belongs to the pancreas in the segmentation output F(x); and repeat the dilation and the substitution until all voxels have been updated.

In some embodiments, when performing the classification process on the mesh model of the pancreas and the mass of the patient to identify a type and a grade of the segmented pancreatic mass, the processor 902 is configured to: encode an initialized feature vector $h_p^0$ for each vertex p; feed the initialized feature vector $h_p^0$ into a graph-based residual convolutional network (Graph-ResNet) to perform the classification process under a pixel level, a vertex level, and a global level; encode a combined feature vector $h^{vp}$; and feed the combined feature vector $h^{vp}$ into a fully connected global classification layer to identify the type and the grade of the segmented pancreatic mass.

In some embodiments, when encoding the initialized feature vector $h_p^0$ for each vertex p, the processor 902 is configured to: obtain a local feature vector $h_p$ of a vertex p in the mesh model by pooling prediction probability maps $F(x)_{w,h,d}$ of a segmentation network F(x) within each receptive field corresponding to each of the four zones Z(p) of the pancreas of the patient, where $F(x)_{w,h,d} \in R^K$, $(w,h,d) \in Z(p)$, and K is a task label indicating a task including a classification task between the masses of the PDAC and the non-PDAC, and a treatment recommendation task; obtain a global feature vector in the mesh model by globally pooling the prediction probability maps $F(x)_{w,h,d}$ of the segmentation network F(x); and concatenate coordinates $(x_p, y_p, z_p)$ of the vertex p, an average edge length $e_p$ between the vertex p and neighbors of the vertex p, a distance $d_p$ between the vertex p and a nearest point at a surface of the segmented pancreatic mass, the local feature vector of each vertex p, and the global feature vector to encode the initialized feature vector $h_p^0$ for each vertex p, where $$e_p = \sum_{p' \in N(p)} e_{pp'} / |N(p)|,$$
$$d_p = \min_r \|p - r\|_2^2,$$
$$p' \in N(p),$$

N(p) is neighboring vertices of the vertex p, and r is a point of the surface of the segmented pancreatic mass.

In some embodiments, when encoding the combined feature vector $h^{vp}$, the processor 902 is configured to: pool four global feature vectors from the four zones of the pancreas according to vertex indices, where the four zones of the pancreas include a pancreas head with the vertex indices 1-48, a ventral body with the vertex indices 49-93, a dorsal body with the vertex indices 94-135, and a pancreas tail with the vertex indices 136-156; and concatenate the four global feature vectors and local feature vectors corresponding to the 156 vertex indices into the combined feature vector $h^{vp}$.

In some embodiments, the Graph-ResNet includes six graph-based convolutional layers and shortcut connections between every two layers. Each of the six graph-based convolutional layers $h_p^{l+1}$ is defined as $h_p^{l+1} = w_0 h_p^l + \Sigma_{p' \in N(p)} w_1 h_{p'}^l$, where $h_p^l$ is a local feature vector attached to the vertex p at a layer l of the Graph-ResNet, and $w_0$ and $w_1$ are learned parameters with $w_1$ being shared by all edges. The Graph-ResNet includes a vertex level loss function $L_{vertex}$, where $L_{vertex} = -\Sigma_p \Sigma_k^K y_{k,p}^v \log(G(h^0)_{k,p})$, $G(h^0)$ is a softmax output of the Graph-ResNet at every vertex, a vertex label $y^v$ is a one-hot encoding of $\hat{y}_p^v$ inferred from a labeled mask, background voxels are labeled as 0, pancreas voxels are labeled as 1, voxels for the segmented pancreatic mass are labeled with a number greater than 1, the vertex p is labeled using a maximum value of the voxels in its corresponding zone Z(p), and $$\hat{y}_p^v = \max_{(w,h,d) \in Z(p)} \hat{y}_{w,h,d}.$$

The fully connected global classification layer includes a loss function $L_{global}$, where $L_{global} = -\Sigma_k^K y_k^g \log(H(h^{vp})_k)$, $H(h^{vp})$ is a softmax output of the fully connected global classification layer, and $y^g$ is a patient level mass/disease label.

The memory 901 may include volatile memory such as random-access memory (RAM), and non-volatile memory such as flash memory, hard disk drive (HDD), or solid-state drive (SSD). The memory 901 may also include combinations of various above-described memories. The processor 902 may include a central processing unit (CPU), an embedded processor, a microcontroller, and a programmable device such as an application-specific integrated circuit (ASIC), a field programmable gate array (FPGA), and a programmable logic array (PLD), etc.

The present disclosure also provides a storage medium storing a computer program. The computer program may be loaded to a computer or a processor of a programmable data processing device, such that the computer program is executed by the computer or the processor of the programmable data processing device to implement the disclosed method.

Although the principles and implementations of the present disclosure are described by using specific embodiments in the specification, the foregoing descriptions of the embodiments are only intended to help understand the method and core idea of the method of the present disclosure. Meanwhile, a person of ordinary skill in the art may make modifications to the specific implementations and application range according to the idea of the present disclosure. In conclusion, the content of the specification should not be construed as a limitation to the present disclosure.

What is claimed is:

1. A method for pancreatic mass diagnosis and patient management, comprising:
   receiving computed tomography (CT) images of a pancreas of a patient during a multi-phase CT scan, the CT images including a plurality of three-dimensional (3D) images of the pancreas for each phase of the multiple phases and the pancreas of the patient including a mass;
   performing a segmentation process on the CT images of the pancreas and the mass to obtain a segmentation mask of the pancreas and the mass of the patient;
   performing a mask-to-mesh process on the segmentation mask of the pancreas and the mass of the patient to obtain a mesh model of the pancreas and the mass of the patient;
   performing a classification process on the mesh model of the pancreas and the mass of the patient to identify a type and a grade of a segmented pancreatic mass, by performing:
   encoding an initialized feature vector $h_p^0$ for each vertex p;
   feeding the initialized feature vector $h_p^0$ into a graph-based residual convolutional network (Graph-ResNet) to perform the classification process under a pixel level, a vertex level, and a global level;
   encoding a combined feature vector $h^{vp}$; and
   feeding the combined feature vector $h^{vp}$ into a fully connected global classification layer to identify the type and the grade of the segmented pancreatic mass; and
   outputting updated CT images of the pancreas of the patient, the updated CT images including the segmented pancreatic mass highlighted thereon and the type and the grade of the segmented pancreatic mass annotated thereon.

2. The method according to claim 1, further comprising: providing a treatment recommendation, based on a degree of malignancy of the segmented pancreatic mass;
wherein:
   the type of the segmented pancreatic mass includes pancreatic ductal adenocarcinoma (PDAC), ampullary cancer (AC), bile duct cancer (DC), pancreatic neuroendocrine tumor (PNET), rare neo-plasma (RARE), solid pseudopapillary tumor (SPT), chronic pancreatitis (CP), intraductal papillary mucinous neoplasm (IPMN), mucinous cystic neoplasm (MCN), and serous cystic neoplasm (SCN);
   the grade of the segmented pancreatic mass includes a low grade, an intermediate grade, and a high grade;
   PDAC, AC, DC, PNET, RARE, and SPT are malignant types, CP, IPMN, and MCN are potentially malignant types, and SCN is a non-malignant type; and
   the patient with the malignant types and the potentially malignant types with the high grade need immediate treatment, the patient with the potentially malignant types with the low and intermediate grades need monitoring, and the patient with the non-malignant type is discharged.

3. The method according to claim 1, further comprising: concatenating the CT images of the pancreas of the patient to form a four-dimensional (4D) input X, wherein $X \in R^{N \times W \times H \times D}$, wherein R represents a matrix, W is an image width, H is an image height, D is an image depth, the multi-phase CT scan is an N-phase CT scan, and N is a positive integer.

4. The method according to claim 3, wherein performing the segmentation process on the CT images of the pancreas and the mass to obtain the segmentation mask of the pancreas and the mass of the patient includes:
   feeding the 4D input X into a segmentation network trained on an input Y which is one-hot encoded by combining a pancreas dataset with masses of radiologist-segmented pancreatic ductal adenocarcinoma (PDAC) and radiologist-segmented non-PDAC, to obtain the segmentation mask of the pancreas;
   wherein $Y \in R^{K \times W \times H \times D}$, K is a task label indicating a task including a classification task between the masses of the PDAC and the non-PDAC, and a treatment recommendation task, the segmentation network includes an nnUNet as a backbone network and a pixel-level segmentation loss function $L_{seg}$, $$L_{seg} = -\sum_{w,h,d} \sum_k^K y_{k,w,h,d} \log(F(x)_{k,w,h,d}) - 2\sum_k^K \frac{\sum_{w,h,d} F(x)_{k,w,h,d} y_{k,w,h,d}}{\sum_{w,h,d} F(x)_{k,w,h,d} + \sum_{w,h,d} y_{k,w,h,d}},$$

F(x) is a softmax output of the nnUNet, and $F(x) \in R^{K \times W \times H \times D}$.

5. The method according to claim 4, wherein performing the mask-to-mesh process on the segmentation mask of the pancreas and the mass of the patient to obtain the mesh model of the pancreas and the mass of the patient includes:
obtaining an initial mesh model including 156 vertices of an average pancreas;
gradually deforming the initial mesh model to fit a surface of the segmentation mask of the pancreas and the mass of the patient to preserve an anatomy of the pancreas of the patient; and
rendering the deformed mesh model to include the 156 vertices distributed in four zones of the pancreas of the patient.

6. The method according to claim 5, wherein obtaining the initial mesh model including the 156 vertices of the average pancreas includes:
obtaining a prototype mesh model based on an average pancreas shape from a training dataset; and
placing 156 vertices equally distributed on a surface of the prototype mesh model to build an anatomic structure including the four zones: a pancreas head, a ventral body, a dorsal body, and a pancreas tail;
wherein the pancreas head includes the $1^{st}$-$48^{th}$ vertices, the ventral body includes the $49^{th}$-$90^{th}$ vertices, the dorsal body includes the 91st-135th vertices, and the pancreas tail includes the $136^{th}$-$156^{th}$ vertices.

7. The method according to claim 5, wherein gradually deforming the initial mesh model to fit the surface of the segmentation mask of the pancreas and the mass of the patient to preserve the anatomy of the pancreas of the patient includes:
guiding the deformation process by a loss function $L_{mesh\text{-}fit}$;
wherein $$L_{meshfit} = \sum_p \min_q \|p-q\|_2^2 + \lambda_1 \sum_e \|e - \text{mean}(e)\|_2^2 + \lambda_2 \sum_e e,$$

p is a vertex in the mesh model, q is a voxel of the surface of the segmentation mask of the pancreas, $\lambda_1=10^{-4}, \lambda_2=10^{-2}$, $e=\|p-p'\|_2$, $p' \in N(p)$, and N(p) are neighboring vertices of the vertex p.

8. The method according to claim 5, wherein rendering the deformed mesh model to include the 156 vertices distributed in the four zones of the pancreas of the patient includes:
dividing the deformed mesh model of the pancreas and the mass of the patient into the four zones Z(p) based on coordinates of 156 vertices of the deformed mesh model, wherein p is a vertex in the deformed mesh model;

labelling a vertex at a coordinate (w,h,d) in a 3D volume A by an index i and a voxel corresponding to the vertex as $A_{w,h,d}$, and setting all other voxels of A to 0, wherein $A \in R^{W,H,D}$, and $A_{w,h,d}=i$;
dilating A by one voxel as A' and substituting each zero voxel in A with a corresponding non-zero voxel in A' that belongs to the pancreas in the segmentation output F(x); and
repeating the dilation and the substitution until all voxels have been updated.

9. The method according to claim 1, wherein encoding the initialized feature vector $h_p^0$ for each vertex p includes:
obtaining a local feature vector $h_p$ of a vertex p in the mesh model by pooling prediction probability maps $F(x)_{w,h,d}$ of a segmentation network F(x) within each receptive field corresponding to each of four zones Z(p) of the pancreas of the patient, wherein $F(x)_{w,h,d} \in R^K$, $(w,h,d) \in Z(p)$, and K is a task label indicating a task including a classification task between the masses of the PDAC and the non-PDAC, and a treatment recommendation task;
obtaining a global feature vector in the mesh model by globally pooling the prediction probability maps $F(x)_{w,h,d}$ of the segmentation network F(x); and
concatenating coordinates $(x_p, y_p, z_p)$ of the vertex p, an average edge length $e_p$ between the vertex p and neighbors of the vertex p, a distance $d_p$ between the vertex p and a nearest point at a surface of the segmented pancreatic mass, the local feature vector of each vertex p, and the global feature vector to encode the initialized feature vector $h_p^0$ for each vertex p, wherein $$e_p = \sum_{p' \in N(p)} e_{pp'} / |N(p)|,$$
$$d_p = \min_r \|p-r\|_2^2,$$
$$p' \in N(p),$$

N(p) is neighboring vertices of the vertex p, and r is a point of the surface of the segmented pancreatic mass.

10. The method according to claim 1, wherein encoding the combined feature vector $h^{vp}$ includes:
pooling four global feature vectors from four zones of the pancreas according to vertex indices, wherein the four zones of the pancreas include a pancreas head with the vertex indices 1-48, a ventral body with the vertex indices 49-93, a dorsal body with the vertex indices 94-135, and a pancreas tail with the vertex indices 136-156; and
concatenating the four global feature vectors and local feature vectors corresponding to the 156 vertex indices into the combined feature vector $h^{vp}$.

11. The method according to claim 1, wherein:
the Graph-ResNet includes six graph-based convolutional layers and shortcut connections between every two layers;
each of the six graph-based convolutional layers $h_p^{l+1}$ is defined as $h_p^{l+1} = w_0 h_p^l + \Sigma_{p' \in N(p)} w_1 h_{p'}^l$, wherein $h_p^l$ is a local feature vector attached to the vertex p at a layer l of the Graph-ResNet, and $w_0$ and $w_1$ are learned parameters with $w_1$ being shared by all edges;
the Graph-ResNet includes a vertex level loss function $L_{vertex}$, wherein $L_{vertex} = -\Sigma_p \Sigma_k^K y_{k,p}^v \log(G(h^0)_{k,p})$, $G(h^0)$ is a softmax output of the Graph-ResNet at every vertex, a vertex label $y^v$ is a one-hot encoding of $\hat{y}_p^v$ inferred from a labeled mask, background voxels are labeled as 0, pancreas voxels are labeled as 1, voxels for the segmented pancreatic mass are labeled with a number greater than 1, the vertex p is labeled using a maximum value of the voxels in its corresponding zone Z(p), and $$\hat{y}_p^v = \max_{(w,h,d) \in Z(p)} \hat{y}_{w,h,d}^v;$$

and the fully connected global classification layer includes a loss function $L_{global}$, wherein $L_{global} = -\Sigma_k^K y_k^g \log(H(h^{v_p})_k)$, $H(h^{v_p})$ is a softmax output of the fully connected global classification layer, and $y^g$ is a patient level mass/disease label.

12. A device for pancreatic mass diagnosis and patient management, comprising:
a memory storing a computer program; and
a processor configured to execute the computer program stored in the memory to:
receive computed tomography (CT) images of a pancreas of a patient during a multi-phase CT scan, the CT images including a plurality of three-dimensional (3D) images of the pancreas for each phase of the multiple phases and the pancreas of the patient including a mass;
perform a segmentation process on the CT images of the pancreas and the mass to obtain a segmentation mask of the pancreas the mass of the patient, wherein the processor is further configured to:
concatenate the CT images of the pancreas of the patient to form a four-dimensional (4D) input X, wherein $X \in R^{N \times W \times H \times D}$, wherein R represents a matrix, W is an image width, H is an image height, D is an image depth, the multi-phase CT scan is an N-phase CT scan, and N is a positive integer,
feed the 4D input X into a segmentation network trained on an input Y which is one-hot encoded by combining a pancreas dataset with masses of radiologist-segmented pancreatic ductal adenocarcinoma (PDAC) and radiologist-segmented non-PDAC, to obtain the segmentation mask of the pancreas, wherein $Y \in R^{K \times W \times H \times D}$, K is a task label indicating a task including a classification task between the masses of the PDAC and the non-PDAC, and a treatment recommendation task, the segmentation network includes an nnUNet as a backbone network and a pixel-level segmentation loss function $L_{seg}$, $$L_{seg} = -\sum_{w,h,d} \sum_k^K y_{k,w,h,d} \log(F(x)_{k,w,h,d}) - 2 \sum_k^K \frac{\sum_{w,h,d} F(x)_{k,w,h,d} y_{k,w,h,d}}{\sum_{w,h,d} F(x)_{k,w,h,d} + \sum_{w,h,d} y_{k,w,h,d}},$$

F(x) is a softmax output of the nnUNet, and $F(x) \in R^{K \times W \times H \times D}$;
perform a mask-to-mesh process on the segmentation mask of the pancreas of the patient to obtain a mesh model including 156 vertices of the pancreas of the patient;
perform a classification process on the mesh model of the pancreas of the patient to identify a type and a grade of a segmented pancreatic mass; and
output updated CT images of the pancreas of the patient, the updated CT images including the segmented pancreatic mass highlighted thereon and the type and the grade of the segmented pancreatic mass annotated thereon.

13. The device according to claim 12, wherein the processor is further configured to:
provide a treatment recommendation, based on a degree of malignancy of the segmented pancreatic mass;
wherein:
the type of the segmented pancreatic mass includes pancreatic ductal adenocarcinoma (PDAC), ampullary cancer (AC), bile duct cancer (DC), pancreatic neuroendocrine tumor (PNET), rare neo-plasma (RARE), solid pseudopapillary tumor (SPT), chronic pancreatitis (CP), intraductal papillary mucinous neoplasm (IPMN), mucinous cystic neoplasm (MCN), and serous cystic neoplasm (SCN);
the grade of the segmented pancreatic mass includes a low grade, an intermediate grade, and a high grade;
PDAC, AC, DC, PNET, RARE, and SPT are malignant types, CP, IPMN, and MCN are potentially malignant types, and SCN is a non-malignant type; and
the patient with the malignant types and the potentially malignant types with the high grade need immediate treatment, the patient with the potentially malignant types with the low and intermediate grades need monitoring, and the patient with the non-malignant type is discharged.

14. The device according to claim 12, wherein when performing the mask-to-mesh process on the segmentation mask of the pancreas of the patient to obtain the mesh model including 156 vertices of the pancreas of the patient, the processor is configured to:
obtain the initial mesh model including 156 vertices of an average pancreas;
gradually deform the initial mesh model to fit a surface of the segmentation mask of the pancreas of the patient to preserve an anatomy of the pancreas of the patient; and
render the deformed mesh model to include the 156 vertices distributed in four zones of the pancreas of the patient.

15. The device according to claim 14, wherein when obtaining the initial mesh model including the 156 vertices of the average pancreas, the processor is configured to:
obtain a prototype mesh model based on an average pancreas shape from a training dataset; and
place 156 vertices equally distributed on a surface of the prototype mesh model to build an anatomic structure including the four zones: a pancreas head, a ventral body, a dorsal body, and a pancreas tail;
wherein the pancreas head includes the $1^{st}$-$48^{th}$ vertices, the ventral body includes the $49^{th}$-$90^{th}$ vertices, the dorsal body includes the $91^{st}$-$135^{th}$ vertices, and the pancreas tail includes the $136^{th}$-$156^{th}$ vertices.

16. The device according to claim 14, wherein when gradually deforming the initial mesh model to fit the surface of the segmentation mask of the pancreas of the patient to preserve the anatomy of the pancreas of the patient, the processor is configured to:

guide the deformation process by a loss function $L_{meshfit}$; wherein $$L_{meshfit} = \sum_p \min_q \|p-q\|_2^2 + \lambda_1 \sum_e \|e - \text{mean}(e)\|_2^2 + \lambda_2 \sum_e e,$$

p is a vertex in the mesh model, q is a voxel of the surface of the segmentation mask of the pancreas, $\lambda_1=10^{-4}$, $\lambda_2=10^{-2}$, $e=\|p-p'\|_2$, $p' \in N(p)$, and N(p) are neighboring vertices of the vertex p.

17. A non-transitory storage medium storing a computer program, when being executed by a processor, the computer program performing:

receiving computed tomography (CT) images of a pancreas of a patient during a multi-phase CT scan, the CT images including a plurality of three-dimensional (3D) images of the pancreas for each phase of the multiple phases and the pancreas of the patient including a mass;

performing a segmentation process on the CT images of the pancreas and the mass to obtain a segmentation mask of the pancreas and the mass of the patient;

performing a mask-to-mesh process on the segmentation mask of the pancreas and the mass of the patient to obtain a mesh model of the pancreas and the mass of the patient;

performing a classification process on the mesh model of the pancreas and the mass of the patient to identify a type and a grade of a segmented pancreatic mass, by performing:

encoding an initialized feature vector $h_p^0$ for each vertex p;

feeding the initialized feature vector $h_p^0$ into a graph-based residual convolutional network (Graph-Res-Net) to perform the classification process under a pixel level, a vertex level, and a global level;

encoding a combined feature vector $h^{vp}$; and feeding the combined feature vector $h^{vp}$ into a fully connected global classification layer to identify the type and the grade of the segmented pancreatic mass; and outputting updated CT images of the pancreas of the patient, the updated CT images including the segmented pancreatic mass highlighted thereon and the type and the grade of the segmented pancreatic mass annotated thereon.

* * * * *